United States Patent
Haider et al.

(10) Patent No.: US 12,377,581 B2
(45) Date of Patent: Aug. 5, 2025

(54) METHOD AND APPARATUS FOR PROCESSING AND/OR RECYCLING OF MATERIALS

(71) Applicant: EREMA ENGINEERING RECYCLING MASCHINEN UND ANLAGEN GESELLSCHAFT M.B.H., Ansfelden (AT)

(72) Inventors: Stephanie Haider, Linz (AT); Michael Aigner, Leonding (AT); Klaus Feichtigner, Linz (AT)

(73) Assignee: EREMA ENGINEERING RECYCLING MASCHINEN UND ANLAGEN GESELLSCHAFT, M.B.H., Ansfelden (AT)

( * ) Notice: Subject to any disclaimer, the term of this patent is extended or adjusted under 35 U.S.C. 154(b) by 927 days.

(21) Appl. No.: 17/271,493

(22) PCT Filed: Aug. 28, 2019

(86) PCT No.: PCT/AT2019/060278
§ 371 (c)(1),
(2) Date: Feb. 25, 2021

(87) PCT Pub. No.: WO2020/041813
PCT Pub. Date: Mar. 5, 2020

(65) Prior Publication Data
US 2021/0197421 A1    Jul. 1, 2021

(30) Foreign Application Priority Data
Aug. 29, 2018 (AT) ............. A 50738/2018

(51) Int. Cl.
G02B 19/00 (2006.01)
B29B 17/00 (2006.01)
(Continued)

(52) U.S. Cl.
CPC ...... *B29B 17/0412* (2013.01); *B29B 17/0036* (2013.01); *G01N 21/255* (2013.01);
(Continued)

(58) Field of Classification Search
CPC ............ B29B 17/0036; G02B 19/0076; G02B 19/0085
See application file for complete search history.

(56) References Cited

U.S. PATENT DOCUMENTS

2006/0136149 A1   6/2006  Long et al.
2012/0024718 A1   2/2012  Foret

FOREIGN PATENT DOCUMENTS

EP    0123771 A1    11/1984
EP    1264170 A     12/2002
(Continued)

OTHER PUBLICATIONS

Examination Report issued in Australian Patent Application No. 2019329926, dated Apr. 9, 2025.
(Continued)

*Primary Examiner* — Joseph P Martinez
(74) *Attorney, Agent, or Firm* — Benesch Friedlander Coplan & Aronoff LLP

(57) ABSTRACT

What is disclosed is a method of processing and/or recycling materials, especially thermoplastic materials,—wherein the material is agitated and mixed in a receivingvessel (1), especially a cutting compressor or a preconditioning unit (PCU), and optionally also heated, comminuted and/or softened, wherein the material in the receiving vessel (1) remains in the form of pieces or particles and unmolten-throughout, and—wherein the material in piece orparticle formbeing agitated within the receiving vessel is subjectedto inline spectroscopic and/or spectrometric analysis and/or
(Continued)

Figure 1:
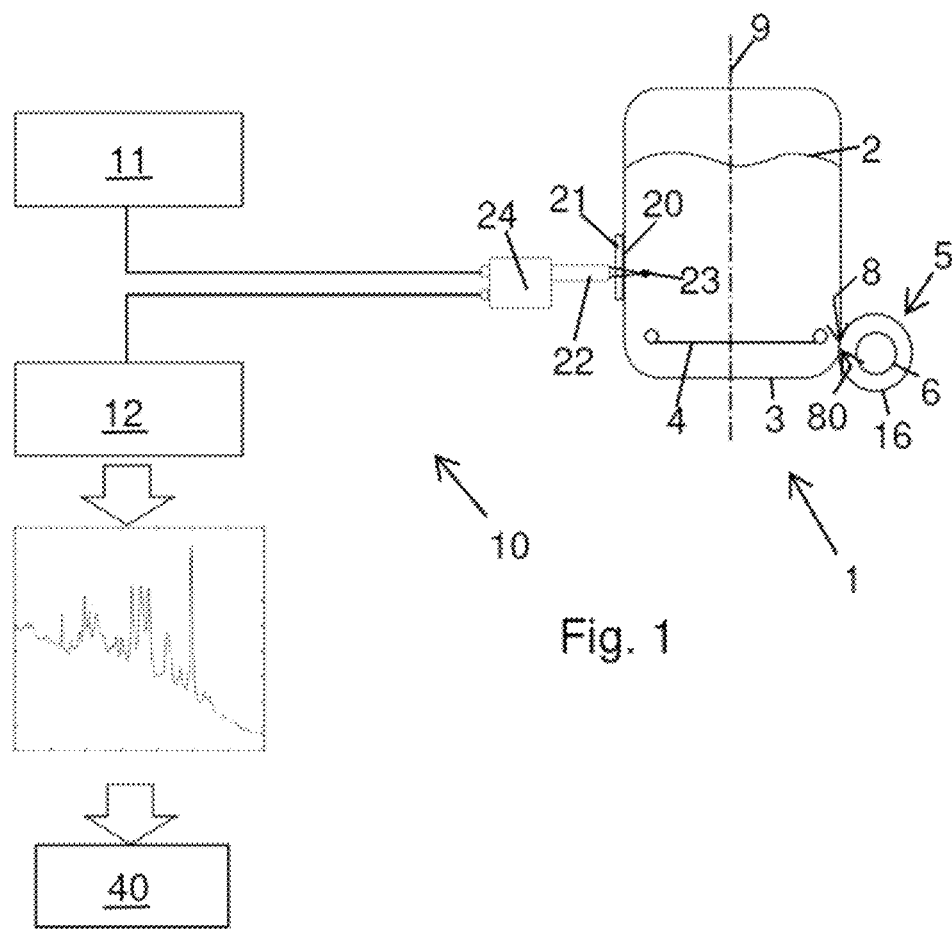

measurement, wherein the measurements ascertained in this way are employed to obtain Information about the material being analysed in each case, especially quantitative and/or qualitative indices of the respective material. Likewise disclosed is an apparatus comprising—at least one receiving vessel (1), especially a cutting compressor, having a mixing and/or comminuting device for the material,—at least one spectroscopic and/or spectrometric measuring apparatus (10) for inline analysis of portions of the material in piece of particle form being agitated within the receiving vessel (1), which is designed to emit a physical Stimulus, especially electromagnetic radiation, for excitation of the rotating material in piece of particle form and—to detect the measurement Signals that arise in reaction to the Stimulus, especially characteristic spectra of the electromagnetic radiation scattered on the material analysed, preferably by spectrometric means, and—a Processing and control unit (40) which is in data communication with the measurement apparatus (10) and is designed—to actuate the measurement apparatus (10), to emit the physical Stimulus, especially electromagnetic radiation, and to detect the resultant measurement Signals and to hold the measurements ascertained in this way available and—optionally, on the basis of the measurements ascertained, to derive and hold available Information concerning the material analysed in each case, especially quantitative and/or qualitative indices of the respective material.

11 Claims, 7 Drawing Sheets

(51) Int. Cl.
*B29B 17/04* (2006.01)
*G01N 21/25* (2006.01)
*G01N 21/31* (2006.01)
*G01N 21/85* (2006.01)
*G01N 33/44* (2006.01)
*G01N 21/84* (2006.01)

(52) U.S. Cl.
CPC ............ *G01N 21/31* (2013.01); *G01N 21/85* (2013.01); *G01N 33/442* (2013.01); *B29B 2017/048* (2013.01); *G01N 2021/8411* (2013.01)

(56) References Cited

FOREIGN PATENT DOCUMENTS

| | | | | |
|---|---|---|---|---|
| EP | 1264170 | B1 * | 4/2009 | ............ G01N 21/85 |
| EP | 2689908 | A1 | 1/2014 | |
| EP | 3128303 | A2 | 2/2017 | |
| EP | 3537119 | A1 | 9/2019 | |
| JP | 62250333 | A | 10/1987 | |
| JP | H10185817 | A | 7/1998 | |
| JP | 3045304 | B2 | 5/2000 | |
| JP | 2002144338 | A | 5/2002 | |
| JP | 2004516163 | A | 6/2004 | |
| JP | 2010208085 | A | 9/2010 | |
| JP | 2017213899 | A | 12/2017 | |
| JP | 07-032363 | B2 | 3/2022 | |
| WO | 2017051424 | A1 | 3/2017 | |

OTHER PUBLICATIONS

Office Action issued in Brazilian Patent Application No. BR 11 2021 003619 9, dated Sep. 1, 2022.
Office Action issued in Japanese Patent Application No. 2021-510399, dated Jan. 31, 2023.
Office Action issued in Korean Patent Application No. 10-2021-7008832, dated Feb. 17, 2025.
Office Action issued in Russian Federation Patent Application No. 2021107712/28, dated Apr. 11, 2023.
Search Report issued in Russian Federation Patent Application No. 2021107712/28, dated Oct. 3, 2023.
Office Action issued in Ukranian Patent Application No. 2021 01528, dated Mar. 15, 2024.

\* cited by examiner

X-X

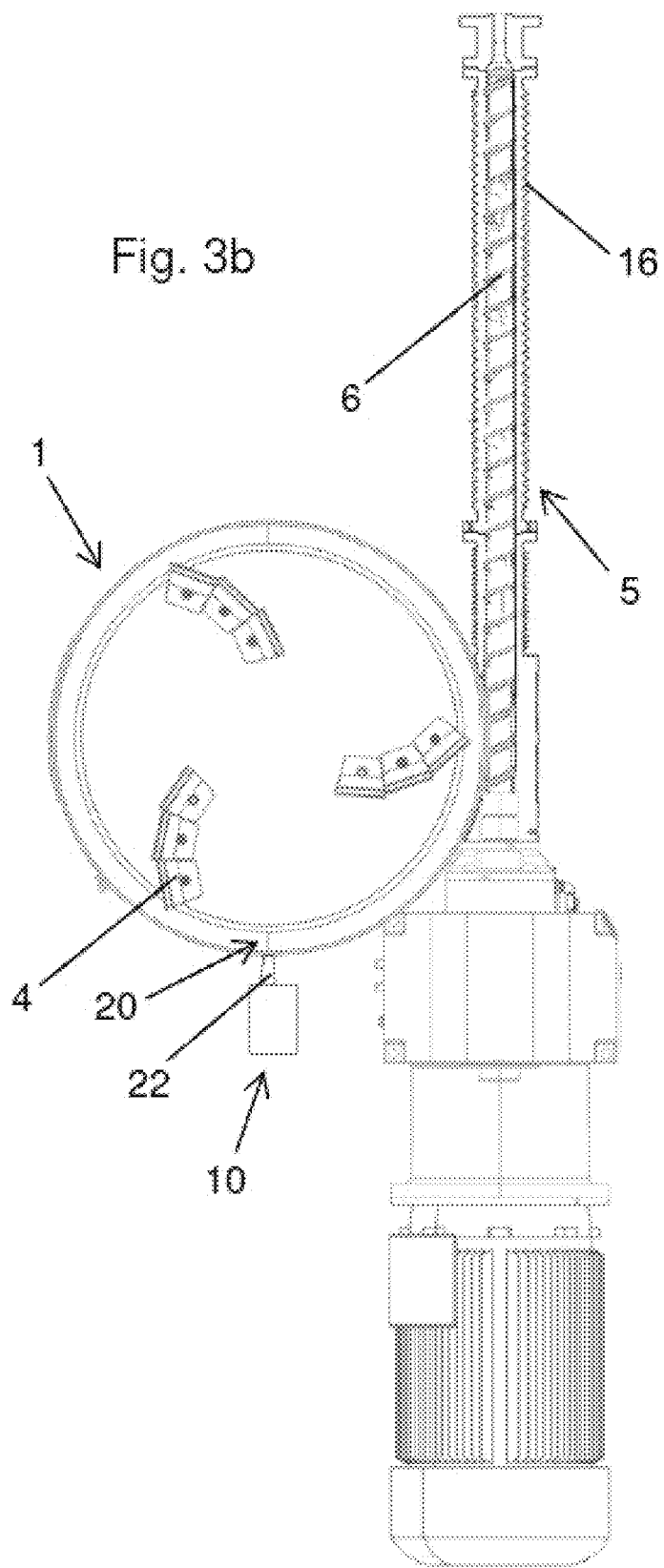

METHOD AND APPARATUS FOR PROCESSING AND/OR RECYCLING OF MATERIALS

The present disclosure relates to a method for preparing, processing and/or recycling of materials, in particular thermoplastic plastic material. The disclosure further relates to a device for carrying out the method according to the present disclosure.

Particularly in the case of plastic recycling, it is a main task to prepare plastics from different sources with possibly different compositions, which may also be unknown. The area of plastic recycling comprises, for example, both the area of internal production waste and the area of the plastic products used, such as packaging, computer housings, or parts from the automotive sector, etc., so that the source materials have, for example, greatly varying filler and polymer contents.

The aim of the preparation is to achieve defined quality characteristics such as defined mechanical, optical and/or other properties for the reuse of the material. In order for these quality characteristics to be achieved, an analysis of the incoming materials as well as the processed materials is necessary in addition to the necessary machinery prerequisite.

It is an object of the present invention to provide a method and a device for preparing, processing and/or recycling of materials such as thermoplastic plastics, with which a preparation of materials with simultaneous possibility of monitoring and controlling the preparation process in order to achieve desired quality characteristics in the process end product is provided in a simple and effective manner.

The present invention achieves this object by a method according to the features of claim 1. According to the invention, it is provided that

- the material is moved and mixed in a receiving container, in particular a cutter compactor or a preconditioning unit (PCU), and, if appropriate, is also heated, comminuted and/or softened, the material in the receiving container remaining lumpy or particulate and unmelted throughout, and
- that the lumpy or particulate material moving inside the receiving container is analyzed or measured inline spectroscopically and/or spectrometrically, the measured values determined in this way being used to obtain information about the material being measured in each case, in particular quantitative and/or qualitative parameters of the respective material.

By means of this configuration of a method according to the invention, it is possible to examine the material moving in the receiving container in an inline spectroscopic and/or spectrometric manner and in this way to obtain information about the material, such as, for example, additive or filler content and polymer composition, so that the processing process can be controlled in accordance with the information, for example by adding fillers or polymers. In this way, desired quality characteristics or properties of the process end product can be precisely adjusted.

In the present case, "inline" is understood to mean that the analysis or measurement of the material in the receiving container is integrated into the preparation and/or processing process line and takes place directly in the line during the preparation and processing of the material.

Hereby it is irrelevant which type of material is to be processed. A method according to the invention or a device according to the invention can also be used for preparing, processing and/or recycling of, for example, food, wood, paper or rock particles, as long as the particles of the lumpy or particulate material as a whole behave like a fluid, i.e. are constantly in motion. The direction of movement is not significant. Thus, the particles in the receiving container can move, for example, in the direction of flow through the receiving container and in the radial direction of the rotating mixing and/or comminuting tools.

A particularly precise examination of the material located in the receiving container can be achieved if at least parts of the lumpy or particulate material located in the interior of the receiving container and rotating there are excited by a physical effect, in particular by electromagnetic radiation, and the measurement signals produced as a reaction to the effect, in particular characteristic spectra of the electromagnetic radiation scattered on the material being measured, are detected, preferably spectrometrically.

In order to be able to use a plurality of different physical processes for identifying chemical substances in the measurement or analysis of the material present in the receiving container, it can be provided that the spectroscopic and/or spectrometric measurement is carried out by means of atomic spectroscopy or molecular spectroscopy. These may be, for example, Raman spectroscopy, NIR spectroscopy, UV/VIS spectroscopy, fluorescence spectroscopy and/or absorption spectroscopy.

In order to ensure a particularly targeted use, for example, of the RAMAN effect, in which energy is transmitted from the light to the matter and vice versa, provision can be made for light in the range of infrared, visible and/or UV light to be used for excitation. In particular, light having a wavelength in the range from 100 to 1400 nm, preferably from 500 to 1000 nm, can be used. In addition or as an alternative thereto, excitation by means of a laser is possible, in particular with a wavelength range from 100 nm to 1400 nm and/or with a power in the range from 15 mW to 5 W, preferably from 100 to 500 mW.

A particularly simple and targeted control of physical properties or quality characteristics in the process end product can be achieved if the detected light is analyzed in order to detect inline specific quantitative and/or qualitative parameters of the material, in particular of the thermoplastic plastic material, or changes in these parameters during the process. This information or parameters can advantageously be used for monitoring and/or controlling the process and/or for controlling the process control in the receiving container. This means that a direct reaction to changes in the parameters during the preparation of the material is possible, for example by adding fillers, so that the properties of the process end product can be controlled in a targeted manner.

In order to be able to measure the detected measurement signals in particularly good quality, i.e. with low background noise, and to keep the excitation source emitting the exciting electromagnetic radiation as small as possible, provision can be made for the electromagnetic radiation exciting the material to be focused on a focal point which is located in the interior of the receiving container at or directly behind the container wall, preferably at a distance of at most 10 cm behind the container wall.

In order to ensure in a particularly reliable manner during the detection of the measurement signals that they are not influenced by surface contamination or coating of the material particles to be measured, provision can be made for a volume range defined by a measurement spot cross-sectional area of 0.1 mm to 5 mm, in particular of 1 mm to 3 mm, and a penetration depth into the material of 0.3 μm to 30 μm, in particular of 8 μm to 15 μm, to be excited by the physical effect, in particular the electromagnetic radiation.

In this way, individual particles can be analyzed, the excitation reaching into deep regions of the respective particle which are not coated, for example, with color, so that a representative measured value for the particle can be obtained.

In order to ensure in a particularly reliable manner that sufficient material to be measured is excited by the physical effect and that the measurement is not influenced by extraneous light, provision can be made for the physical effect exciting the material, in particular the electromagnetic radiation, to be introduced into the interior of the receiving container or into the material at one or more of the following positions:

below the filling level of the material or material particles in the receiving container during operation, at a height and/or at a distance from the bottom or from the mixing and/or comminuting tool, in which the physical effect, in particular the electromagnetic radiation, is constantly below the method-defined predetermined filling level of the material particles located or rotating in the receiving container and/or below the level of the mixing stream formed during a movement and/or rotation of the material particles, at the level of the middle third range of the method-defined predetermined filling level of the material in the receiving container and/or the mixing stream, in that region of the receiving container in which the density of the moving and/or rotating material particles is highest; and/or in that region of the receiving container in which the moving and/or rotating material particles exert the highest pressure on the side wall of the receiving container.

A particularly frequent and regular exchange of the material at the measuring position or at the focal point can be achieved if the lumpy or particulate material in the outer region of the receiving container, in particular at the side wall of the receiving container, has a direction of movement in the circumferential direction and/or a predominantly upwardly directed direction of movement.

A further improvement in the exchange of material at the measuring position or at the focal point can be ensured if the lumpy or particulate material rotates radially at a speed of 0.3 m/s to 45 m/s and/or in the vertical direction at a speed of 0.1 m/s to 60 m/s. In this way, it can be achieved that the lumpy or particulate material is exchanged frequently and regularly in the outer region of the receiving container, in particular on the side wall of the receiving container.

A particularly exact possibility for deriving information about the material located in the interior of the receiving container can be provided if the lumpy or particulate material located in the interior of the receiving container and rotating there, in particular individual particles of the material, is excited at a plurality of predetermined times by a physical effect, in particular electromagnetic radiation, and the mean value of the information about the respectively measured material, in particular about the individual particles, is determined and kept available. This can preferably be the mean value of the quantitative and/or qualitative parameters of the respective material or of the respective particles, which have been determined on the basis of selected, preferably all, measured values determined at these times. Thus, a mean value is obtained from the measured values of the individual measured particles.

A further particularly precise possibility for obtaining information about the material located in the interior of the receiving container, in which at the same time a physical effect, which is emitted by an excitation source with particularly low power, is also sufficient, can be provided if the lumpy or particulate material located in the interior of the receiving container and rotating there is continuously excited by a physical effect, in particular electromagnetic radiation, for a predetermined period of time, in particular of several seconds. For the respective period of time, common information about the material measured in each case, in particular a quantitative and/or qualitative parameter, is calculated and kept available on the basis of the measured values determined continuously within this period of time. This results in a cumulative measurement value for all particles which have moved past the measurement position or the focus point during the measurement period.

In order to be able to correct effects caused by temperature changes which could falsify the measurement signals emanating from the material to be measured or the associated information about the material in a particularly effective manner, provision can be made for the temperature in the interior of the receiving container and/or the temperature of the material to be measured and for the temperature information to be included in the evaluation. The measured temperature information can serve as an indication for the correction of the information about the respectively measured material, in particular the quantitative and/or qualitative parameters of the respective material. In addition or as an alternative to this, the material temperature can be detected and used as a specification for the correction of the spectra.

A particularly accurate evaluation of the information determined for the material can be ensured if reference information, in particular quantitative and/or qualitative reference parameters, preferably reference spectra, are stored and the information determined for the respectively measured material, in particular the parameters, preferably the spectra, are compared with the reference information, in particular the reference parameters, preferably the reference spectra. The deviation from the reference information, in particular the reference parameters, preferably the reference spectra, can thus be determined in a particularly simple manner, and in particular displayed and/or used for monitoring and/or controlling the process control in the receiving container and/or the subsequent process chain.

It is also an object of the invention to provide a device for carrying out a method according to the invention for preparing, processing and/or recycling of materials, in particular thermoplastic plastic materials.

According to the invention, it is provided that the device comprises at least one receiving container, in particular a cutter compactor and/or a preconditioning unit (PCU), with a mixing and/or comminuting device for the material and with a spectroscopic and/or spectrometric measuring device for analyzing the lumpy or particulate material moving in the interior of the receiving container or for obtaining information about the material measured in each case, in particular quantitative and/or qualitative parameters of the respective material.

This configuration of a device according to the invention makes it possible to carry out a spectroscopic and/or spectrometric measurement or analysis of the material moving in the receiving container inline. Thus, information about the material, such as additive or filler content and polymer composition, can be determined inline, so that the processing process can be controlled in accordance with the information in order to precisely set desired quality characteristics or properties for the process end product, for example by adding fillers or polymers.

A particularly compact embodiment of a device according to the invention, which enables the material to be processed to be measured and analyzed inline, can be provided if it comprises at least one receiving container, in particular a cutter compactor, with a mixing and/or comminuting device for the material, at least one spectroscopic and/or spectrometric measuring device for the inline measurement of parts of the lumpy or particulate material moving in the interior of the receiving container, and a processing and control unit in data communication with the measuring device.

In this case, the measuring device is advantageously designed to emit a physical effect, in particular electromagnetic radiation, to excite the rotating lumpy or particulate material and to detect, preferably spectrometrically, the measuring signals arising in response to the action, in particular characteristic spectra of the electromagnetic radiation scattered on the measured material.

In this case, the processing and control unit is advantageously designed to control the measuring device, to emit the physical effect, in particular electromagnetic radiation, and to detect the resulting measuring signals and to keep the measured values determined in this way available and, if appropriate, to derive and keep available information about the respectively measured material, in particular quantitative and/or qualitative parameters of the respective material, on the basis of the determined measured values.

A receiving container which is particularly suitable for preparing, processing or recycling of materials can be provided if the receiving container has a side wall and is essentially conical or cylindrical or has a conical or cylindrical wall section and, if appropriate, also has a lower bottom surface.

Particularly efficient preparation of a wide variety of materials can be ensured if at least one rotating mixing and/or comminuting tool for moving and mixing, and optionally also for heating, comminuting and/or softening, of the lumpy or particulate material to be prepared is arranged in the receiving container as a mixing and/or comminuting device, in particular rotatable about a vertical axis of rotation, wherein a vortex and/or a mixing stream can be formed in operation in the receiving container.

In applications in which excessive mixing of the particles is undesirable, it can thus advantageously be achieved that the material forms a vortex and rotates largely only in one plane, while along the longitudinal axis of the receiving container the material passes, for example, at a speed of 2 m/h at a circumferential speed of, for example, approximately 0.3 m/s. In applications in which particularly good mixing is desired, a mixing stream can be formed.

Particularly effective preparation of the materials in the receiving container can be achieved if the circumferential speed of the mixing and/or comminuting tool is selected such that the lumpy or particulate material rotates radially at a speed of 0.3 to 45 m/s and/or in the vertical direction at a speed of 0.1 to 60 m/s. In this way, it is advantageously also ensured that the material is constantly exchanged at the measuring position or the focal point.

A particularly simple discharge of prepared materials from the receiving container can be ensured if an opening is formed in the receiving container, in particular in a side wall of the receiving container, through which opening the pretreated plastic material can be discharged from the interior of the receiving container, and if at least one conveyor, in particular an extruder, is arranged with at least one screw rotating, in particular plasticizing or agglomerating, in a housing for receiving the pretreated material emerging from the opening.

For a further simplification of the discharge, the opening in the receiving container can be located in the region of the height of the lowest mixing and/or comminuting tool which is closest to the bottom, and the housing can have a feed opening, which is located on its end face or in its casing wall, for the material to be gripped by the screw and which is connected to the opening.

A particularly compact embodiment of the measuring device of a device according to the invention can be provided if the measuring device comprises at least one excitation source which acts or is directed into the interior of the receiving container for emitting a physical effect, in particular electromagnetic radiation, on at least parts of the lumpy or particulate material which is located in the interior of the receiving container during operation and rotates there, and at least one detector, in particular a spectroscope, for detecting the measuring signals which arise in response to the effect, in particular characteristic spectra of the electromagnetic radiation scattered on the measured material.

In this case, the excitation source can act, for example, from the direction of the container wall of the receiving container or starting from the mixing and/or comminuting tool or from the bottom surface of the receiving container into the interior of the receiving container.

A particularly reliable characterization of the material particles located in the receiving container can be achieved if the processing and control unit is designed for spectrometric and/or spectroscopic analysis of the measurement signals arising in response to the action, in particular of characteristic spectra of the electromagnetic radiation scattered on the measured material.

A particularly simple possibility of avoiding disturbing influences on the excitation source and/or the detector of the measuring device of a device according to the invention emanating from the receiving container can be provided if the excitation source and/or the detector and/or the processing and control unit are physically spaced apart from the receiving container or are coupled to the receiving container in a vibration-free manner, in particular via fiber-optic systems and/or light guides.

In order to be able to utilize a wide variety of physical processes for excitation and chemical analysis of the material present in the receiving container, it can be provided that the measuring device comprises a device, in particular a detector, for atomic spectroscopy or molecular spectroscopy, in particular for Raman spectroscopy, NIR spectroscopy, UV/VIS spectroscopy, fluorescence spectroscopy and/or absorption spectroscopy.

In order to be able to analyze or characterize the material inside the receiving container on the basis of its reaction to light in different wavelength ranges, provision can be made for the excitation source to be designed such as to emit light in the range of infrared, visible and/or UV light, in particular in the range from 100 to 1400 nm, preferably from 500 to 1050 nm.

A particularly versatile excitation source can be provided if the excitation source is a laser, in particular with a wavelength range from 100 nm to 1400 nm and/or a power in the range from 15 mW to 5 W, preferably from 100 mW to 500 mW.

A particularly reliable measurement of the materials inside the receiving container with simultaneous physical separation of the receiving container from the measuring device, so that the measuring device remains largely unaffected by disturbing influences emanating from the receiving container, can be provided if at least one measuring opening is provided in the receiving container, in particular in the side wall of the receiving container. In this case, the measuring opening is designed in such a way that the physical effect emitted by the excitation source, in particular the emitted electromagnetic radiation, acts on the material in the receiving container and scattered light from the receiving container can be detected outside the receiving container.

A measuring opening which causes particularly slight structural changes to the receiving container, which could cause a static weakening of the receiving container, can be provided if the measuring opening has a diameter of 0.5 to 100 mm.

In order to be able to record the measurement signals emanating from the material in the interior of the receiving container in a largely unadulterated manner, provision can be made for the measurement opening to be closed by a window made of material, for example sapphire glass, which is transparent, in particular to electromagnetic radiation.

In order to ensure the smallest possible falsification of the measurement signals emanating from the material in the interior of the receiving container, provision can furthermore be made for the window to have a thickness of 1 to 100 mm.

In order to influence the stability of the receiving container as little as possible by the arrangement of a window or a measuring opening which is closed by a window, provision can be made for the surfaces of the window to be planar and aligned parallel to one another. Alternatively, this effect can be achieved if the inner surface of the window facing the receiving container is adapted concavely to the radius of the receiving container and the outer surface of the window facing away from the receiving container is formed parallel concavely to the inner surface.

In order to achieve in a particularly reliable manner that sufficient material is transported past the measuring opening, provision can be made for the at least one measuring opening, in particular in the side wall of the receiving container, to be arranged at one or more of the following positions:
  in the region of the height of the lowest mixing and/or comminuting tool closest to the bottom, in particular somewhat above or below it, preferably at the narrowest distance between the outermost point of the mixing and/or comminuting tool and the side wall, and/or
  in the region of the lower third of the height of the receiving container.

A particularly advantageous positioning of the measuring opening, which ensures a particularly accurate analysis or measurement of the material located in the interior of the receiving container, can be achieved if the at least one measuring opening, in particular in the side wall of the receiving container, is/are arranged at one or more of the following positions:
  below the filling level of the material or material particles in the receiving container during operation,
  at a height and/or at a distance from the bottom or from the mixing and/or comminuting tool, in which the physical effect, in particular the electromagnetic radiation, is constantly below the method-defined predetermined filling level of the material particles located or rotating in the receiving container and/or below the level of the mixing stream formed during a movement and/or rotation of the material particles,
  at the level of the middle third range of the method-defined predetermined filling level of the material in the receiving container and/or the mixing stream,
  in that region of the receiving container in which the density of the moving and/or rotating material particles is highest; and/or
  in that region of the receiving container in which the moving and/or rotating material particles exert the highest pressure on the side wall of the receiving container.

At all these positions, it is ensured that sufficiently frequently changing material moves past the measuring opening and that the measurement is not influenced by extraneous light.

A particularly low influence on the measurement signals emanating from the measured material by, for example, coatings or soiling on the surface of the material particles can be achieved, if the volume range that can be excited by the physical effect, in particular the electromagnetic radiation, is defined by a measurement spot cross-sectional area of 0.1 mm to 5 mm, in particular of 1 mm to 3 mm, and a penetration depth into the material of 0.3 µm to 30 µm, in particular of 8 µm to 15 µm.

A particularly favorable signal-to-noise ratio of the measurement signals can be achieved if a lens or a lens system is provided for focusing the electromagnetic radiation of the excitation source onto a focal point, the focal point being formed in particular at or directly behind the window, preferably at a distance of at most 10 cm behind the window.

A particularly targeted control of the preparation or recycling process of the materials, in particular of the thermoplastic plastic materials, can be achieved if the processing and control unit cooperates with a process control unit and is in data communication with the latter. Such a process control unit is advantageously designed to use data transmitted by the processing and control unit, in particular information about the respectively measured material, preferably quantitative and/or qualitative parameters of the respective material, for monitoring and/or controlling the process control in the receiving container and/or the subsequent process chain.

Particularly effective control of the quality characteristics or of the desired e.g. optical or physical properties of the process end product can be ensured if the process control unit is designed, on the basis of the data transmitted by the processing and control unit, to
  carry out a dosing of fillers into the receiving container and/or
  feed materials, in particular polymers, into the receiving container and/or into a discharge device connected to the receiving container, and/or
  to discharge processed materials, in particular granules, from the receiving container by means of the discharge device connected to the receiving container.

A particularly simple consideration of temperature influences which can influence the measuring signals emitted by the material to be measured can be provided if at least one temperature measuring device is provided upstream of the processing and control unit. Such a temperature measuring device is designed to measure the temperature inside the receiving container and/or the temperature of the material and to transmit it to the processing and control unit. In this case, the processing and control unit is advantageously designed to use the measured values determined by the at least one temperature measuring device for correcting the temperature influence on the information determined for the respective material measured, in particular the temperature-dependent characteristic spectra of the electromagnetic radiation scattered on the material measured, and to keep the information corrected in this way, in particular spectra, available.

A particularly exact correction of temperature influences can be achieved if the temperature measuring device is arranged in the receiving container at the same height, in particular at the same position, as the at least one measuring opening.

A possibility of obtaining particularly reliable information about the material located in the interior of the receiving container can be provided if the processing and control unit is designed to:

drive the measuring device, in particular the excitation source, at a plurality of predetermined times, to repeatedly emit a physical effect, in particular electromagnetic radiation, and to calculate and keep available the mean value of the information about the material measured in each case, in particular about the individual particles measured, preferably the quantitative and/or qualitative parameters of the material in question, which were determined on the basis of selected, preferably all, measured values determined at these times by the measuring device, in particular the detector.

A further possibility of deriving particularly reliable information about the material inside the receiving container, in which advantageously an excitation source with particularly low power is sufficient, can be provided if the processing and control unit is designed to:

drive the measuring device, in particular the excitation source, to continuously emit a physical effect, in particular electromagnetic radiation, for a predetermined period of time, in particular of several seconds, and to calculate and keep available, for the respective period of time, common information about the respectively measured material, in particular a quantitative and/or qualitative parameter, on the basis of the measured values continuously determined by the measuring device, in particular the detector, within this period of time.

A particularly simple evaluation or analysis of the information determined by the processing and control unit, such as spectra, can be provided if the processing and control unit comprises a memory, reference information, in particular quantitative and/or qualitative reference parameters, preferably reference spectra, being stored in the memory, and if the processing and control unit is designed to compare the information determined for the respectively measured material, in particular the parameters, preferably the spectra, with the reference information, in particular the reference parameters, preferably the reference spectra, and to determine the deviation from the reference information, in particular the reference parameters, preferably the reference spectra, and in particular to forward it to the process control unit and/or a display unit.

In the present case, a measuring device is understood to mean a device for recording or displaying and quantitative and/or qualitative analysis of a spectrum which comprises an excitation source and a detector. The excitation source and the detector are thereby matched to one another. Such a measuring device can be a spectrometer.

In the present case, a detector is understood to mean a device for detecting and decomposing radiation or other physical measured values into a spectrum, which detector can be integrated in a measuring device. Such a detector can be a spectroscope.

Further advantages and configurations of the invention emerge from the description and the attached drawings.

The invention is represented schematically below in the drawings on the basis of particularly advantageous exemplary embodiments that are to be understood as non-limiting and is described by way of example with reference to the drawings.

Figure 2:
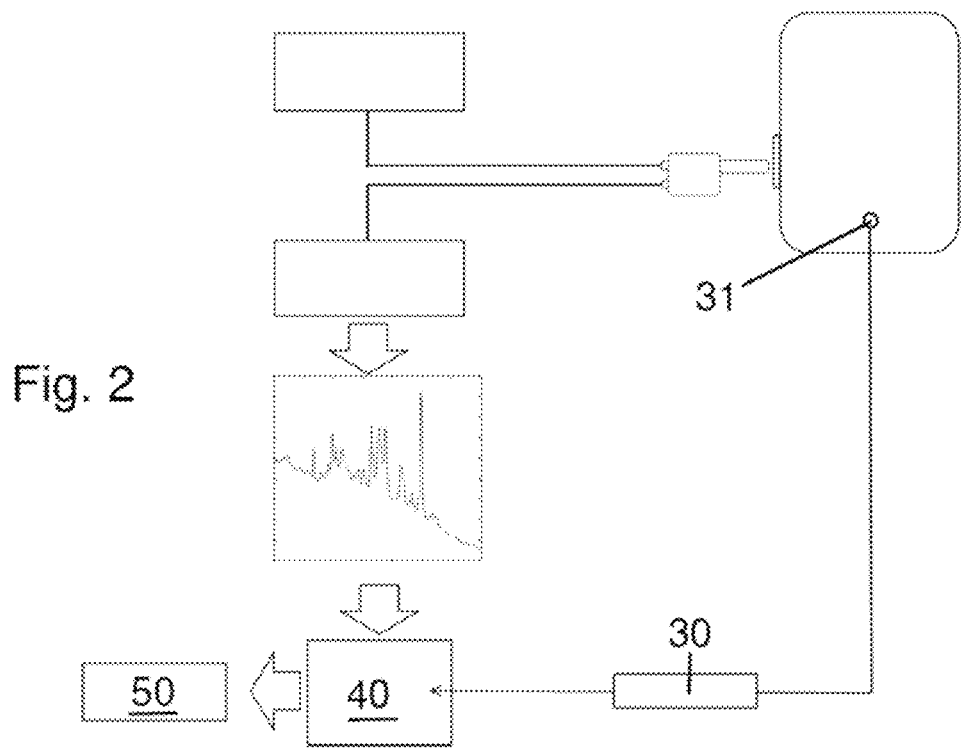
Figure 3A:
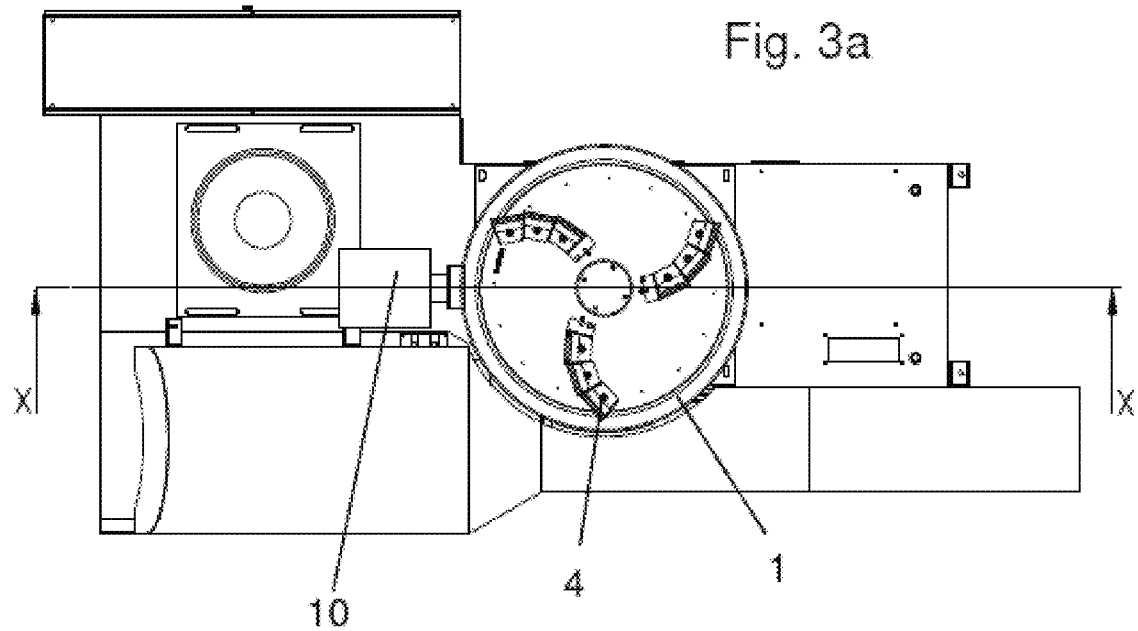
Figure 4:
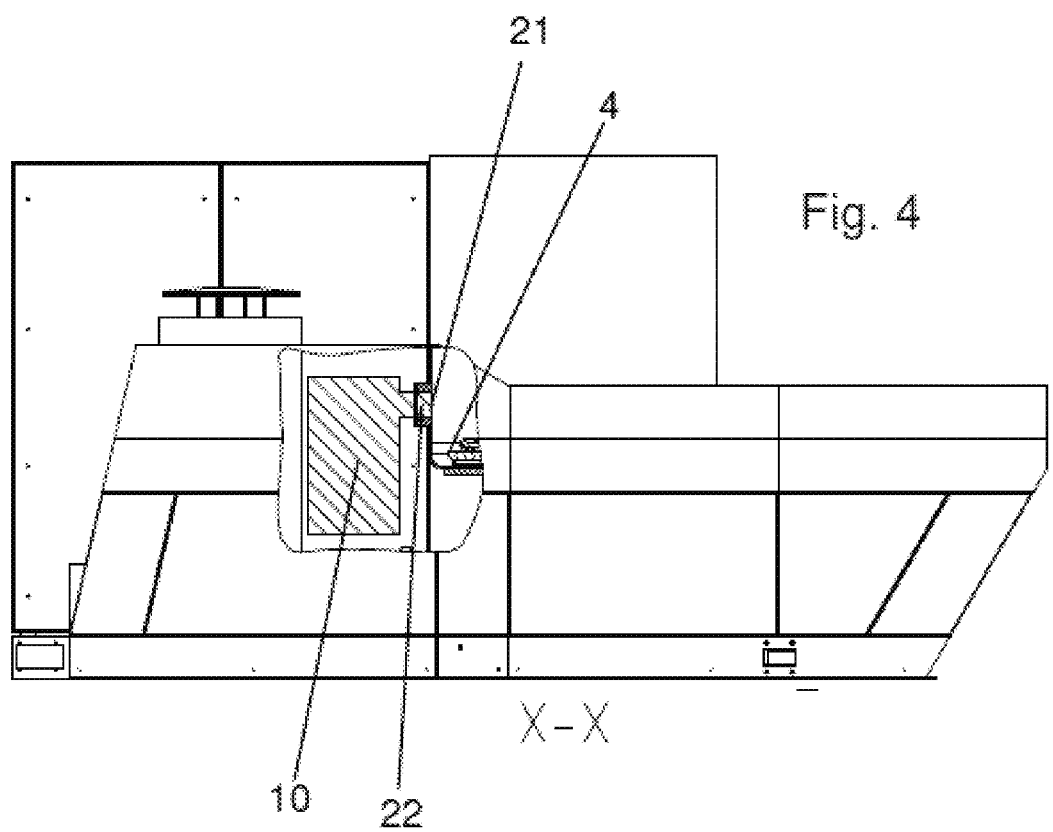
Figure 5:
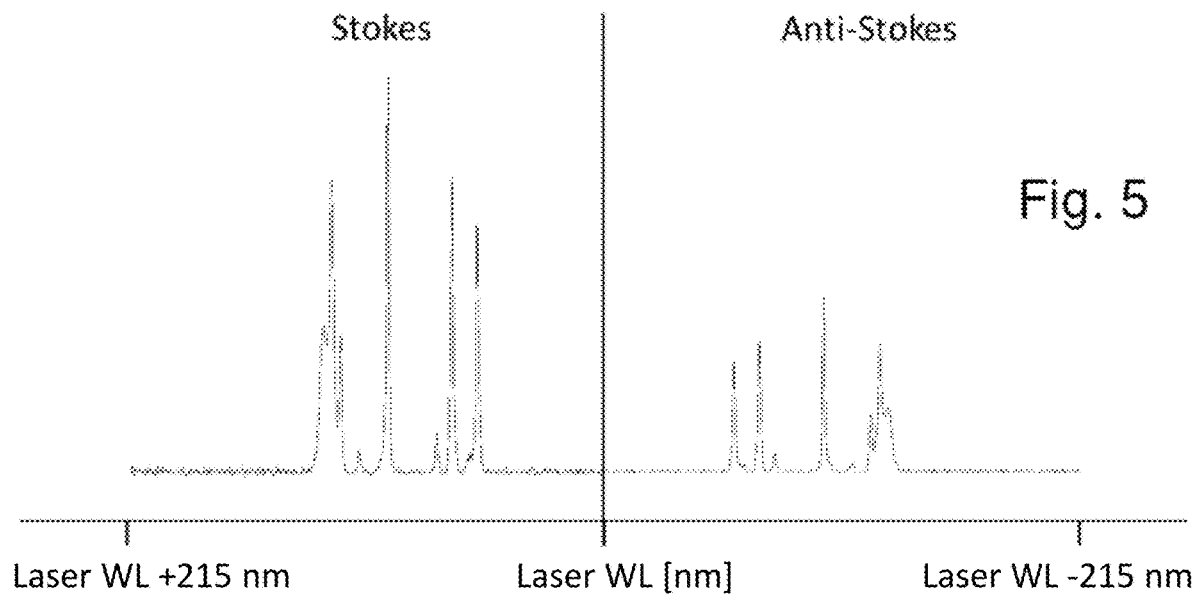
Figure 6:
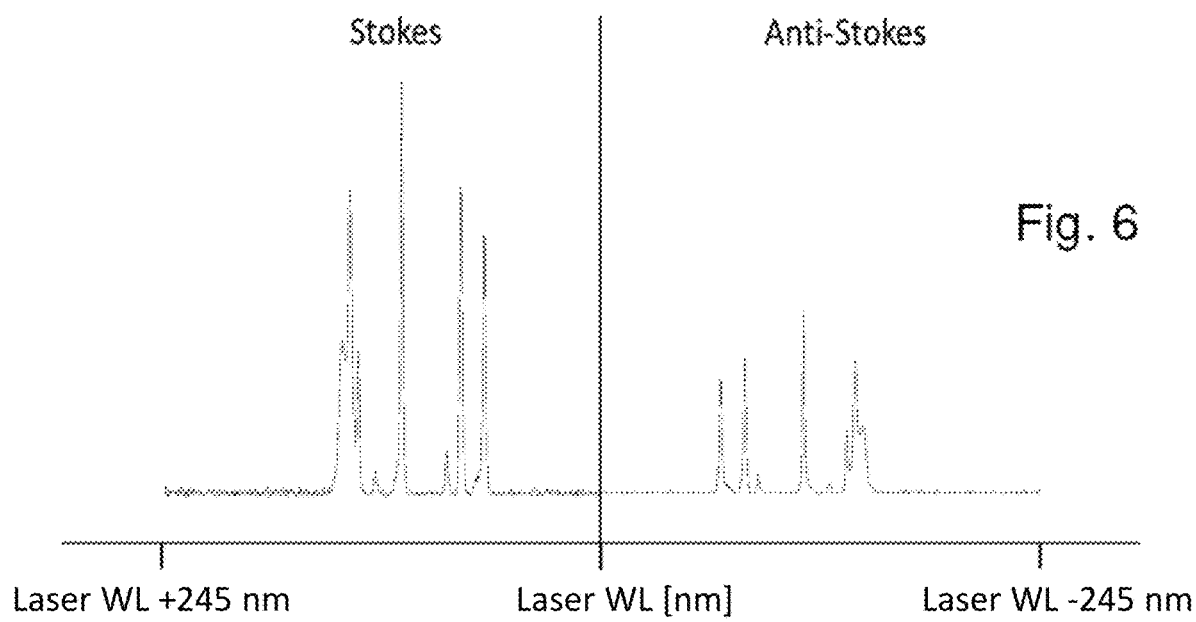
Figure 7:
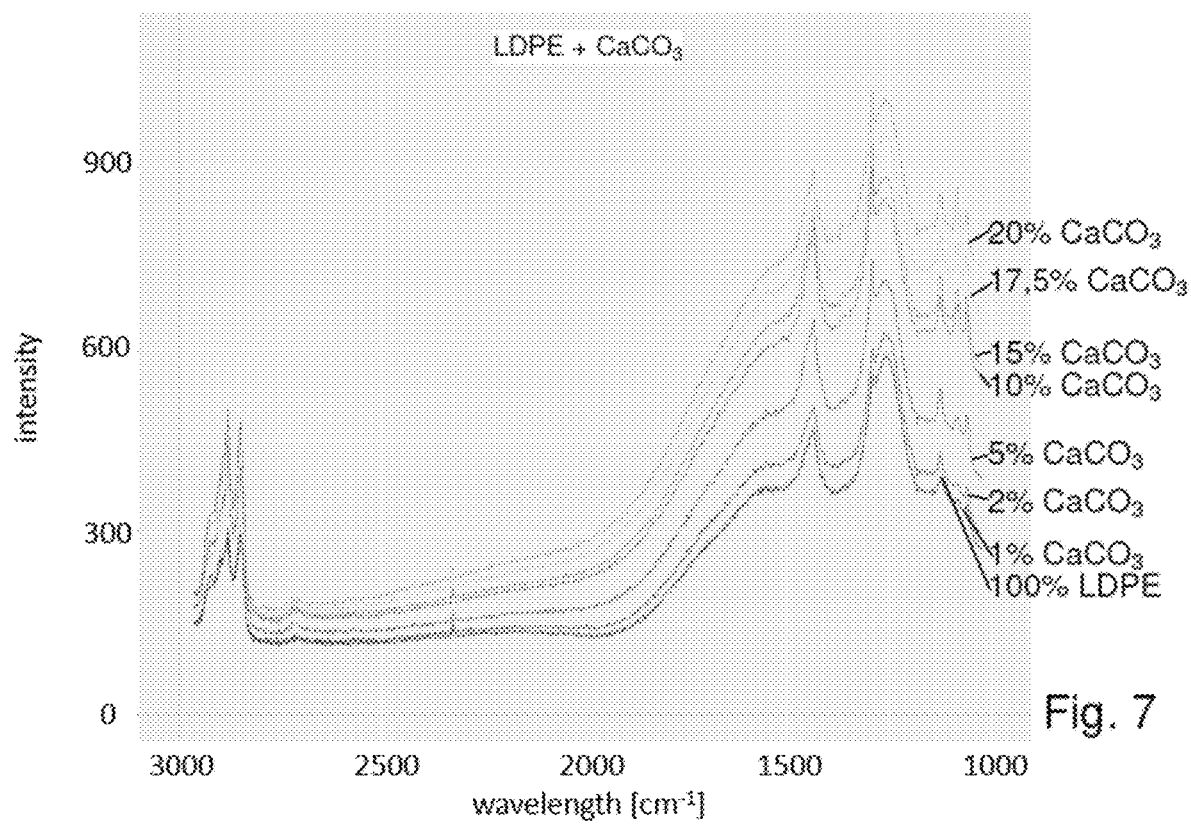
Figure 8:
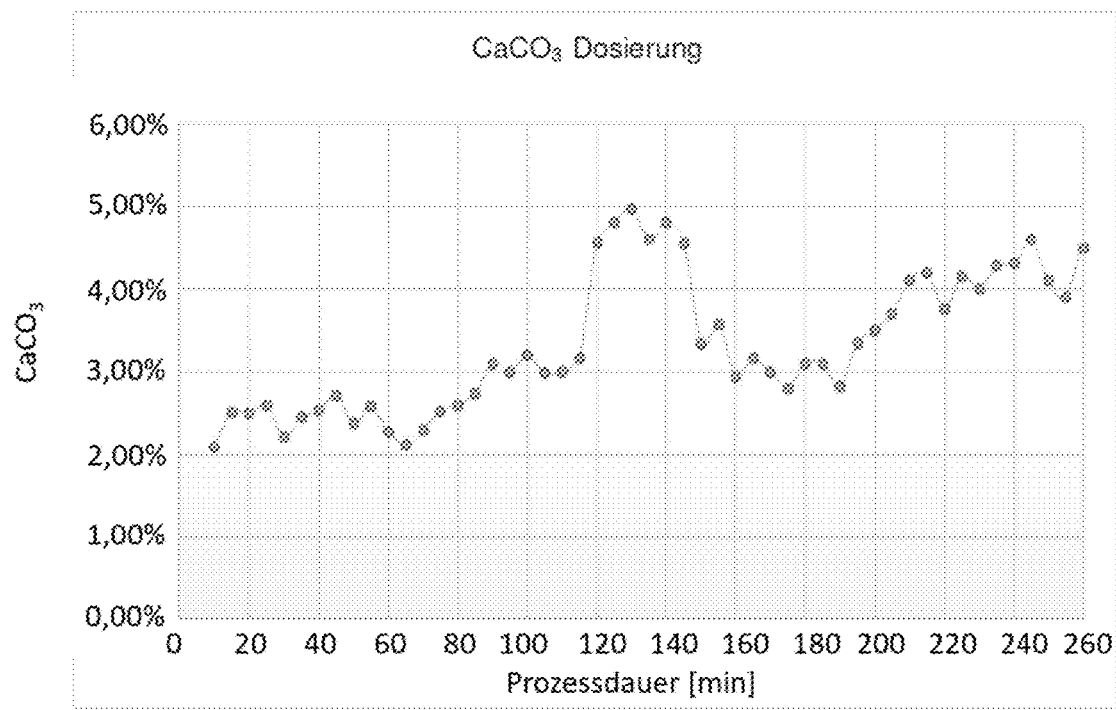
Figure 9:
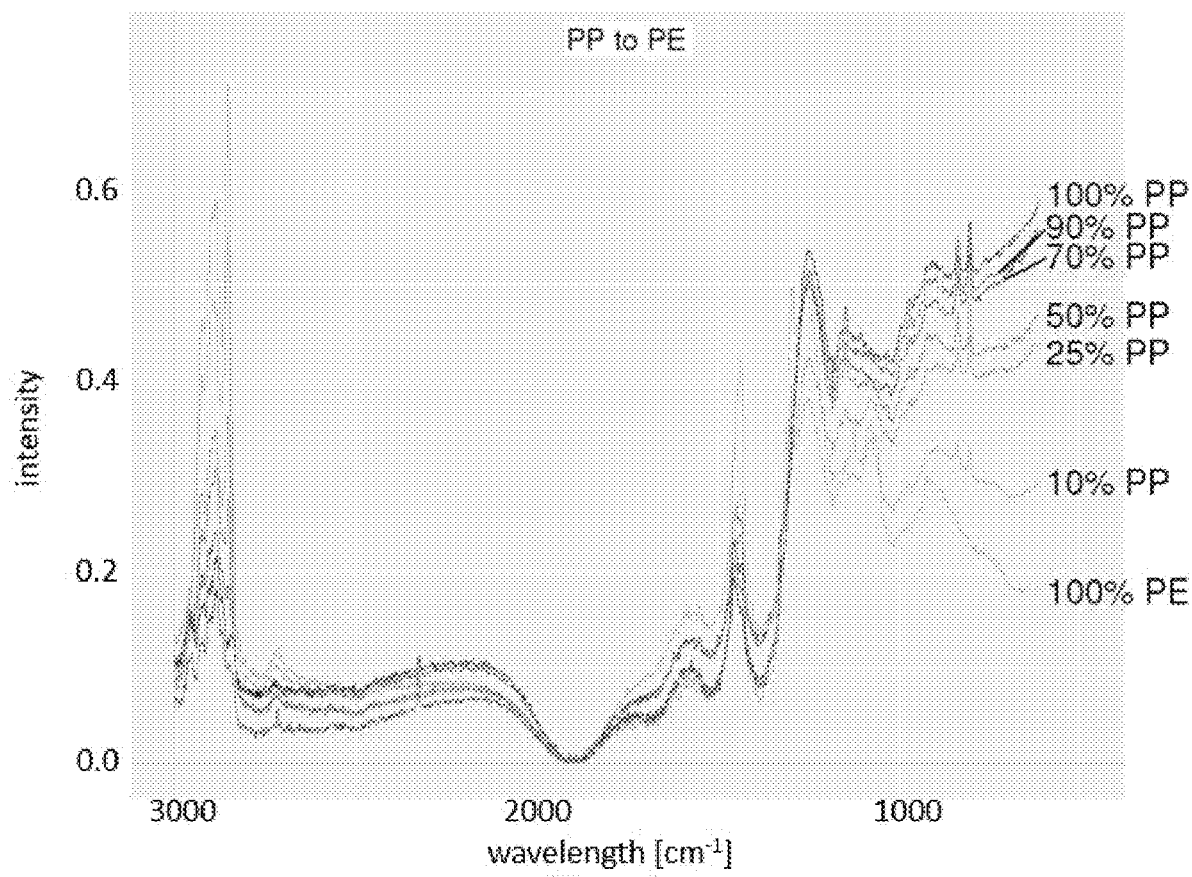
Figure 10:
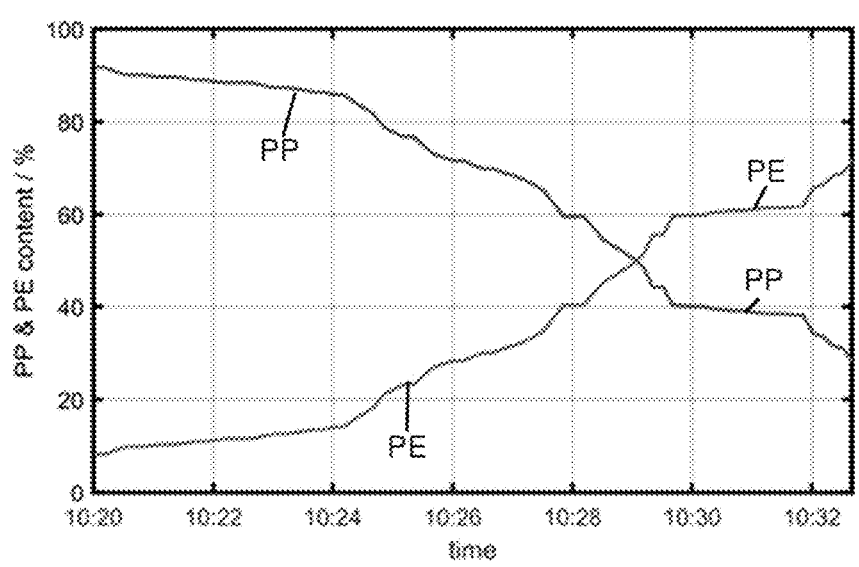
Figure 11:
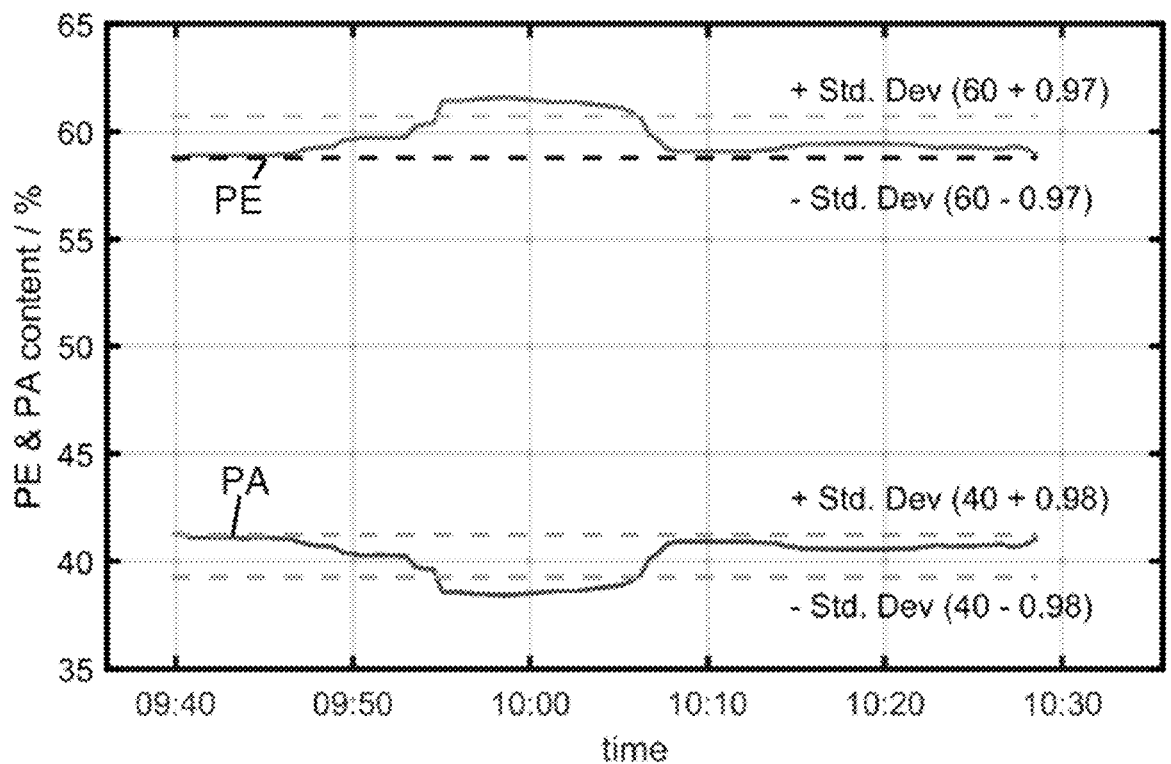

They schematically show the following:

FIG. 1 shows an exemplary embodiment of a device according to the invention for preparing, processing and/or recycling materials, in particular thermoplastic plastic materials, with a RAMAN spectrometer connected to a receiving container, FIG. 2 shows an exemplary embodiment of the device of FIG. 1 with a temperature measuring device, FIG. 3a, FIG. 3b and FIG. 4 show further illustrations of the coupling of a measuring device to a receiving container, FIG. 5 and FIG. 6 show examples of Stokes and Anti-Stokes lines at different wavelengths, FIG. 7 shows recorded spectra of LPDE material with different contents of $CaCO_3$ as filler, FIG. 8 shows the variation of the $CaCO_3$ content over the process duration derived from the spectra in FIG. 7, FIG. 9 shows recorded spectra of for mixtures of PP and PE materials with different compositions, FIG. 10 shows the PP and PE content determined on the basis of the spectra from FIG. 9 for different measuring times, FIG. 11 shows the PA and PE content determined on the basis of spectra for different measuring times.

GENERAL

A substantial part of the preparation of the thermoplastic or partially thermoplastic materials is taken over by the cutter compactor during operation of a cutter-compactor-extruder combination, i.e. an assembly of a cutter-compactor, a so-called "preconditioning unit" PCU, with an extruder. Such a cutter compactor or such a preconditioning unit PCU is referred to below as receiving container 1.

In this case, a receiving container 1 is an essentially cylindrical container which can contain a mixing and/or comminuting device, i.e., for example, stirring-cutting circulating tools, which are constructed primarily from below or from the point next to a conveyor, for example, an extruder 5, upwards. The tools can be designed as cutting, stirring, mixing or as combinations thereof. Such devices are known, for example, from EP 2 689 908 B1 or EP 2 525 953 B1 or EP 123 771.

The material to be processed behaves essentially like a fluid. It is either already present in a lumpy shape or it is brought into such a lumpy shape by the tools. By cutting, stirring and/or mixing, energy is introduced into the material and the material is heated uniformly, complete heating being achieved irrespective of the thickness of the material particles. By softening, by regression of the stretching, the bulk density can increase. Furthermore, heating creates the prerequisite that volatile substances, some of which are undesirable, can escape more easily. Furthermore, depending on the type of thermoplastic polymer, structural changes, for example a change in crystallization, may result.

The finished prepared material can then be discharged from the receiving container 1 either continuously or also in batches. Suitable discharge devices or conveyors are flaps, conveyor screws or extruder screws which are mounted in such a way that the material is discharged at least by the pure centrifugal force. However, forced discharge by tilting or falling is also possible. Furthermore, a conveying tool can also be introduced into the receiving container 1 and the pretreated material can be discharged. For continuous operation, the preferred variant is a continuous discharge of the material.

Physical methods, which are based on the interaction between a physical effect such as electromagnetic radiation and matter and which, for example, analyze the energy spectrum of a sample on the basis of radiation or waves, such as frequency spectrum analysis methods such as NIR, RAMAN, MIR etc. have long been discussed in plastics recycling. In connection with the invention, such physical methods are understood to mean methods for identifying chemical substances by physical excitation, such as, for example, by a laser. This excitation excites processes such as rotation, oscillation, phonon or spin flip and these lead to a change in the charge carrier density, which can be used to identify chemical substances.

In some cases, such physical methods are used in sorting processes in plastic recycling. In optical sorting systems, for example, FT-NIR is used to separate different types of plastics. Essentially, a lumpy separated material is present here, which is sorted out according to the good/bad principle. Similar systems are used in the laboratory or for material identification as hand-held devices.

In extrusion technology, methods of this type have hitherto only been used experimentally for melt and property characterization of ingredients, since the statistical prerequisites, i.e. a small measuring range, long measuring times, low homogenization in the case of polymer mixtures, low penetration depth into the melt, and the wall adhesion occurring in the case of many polymers, i.e. the material is not exchanged, allow statements to be made, primarily only for a single polymer in a reasonable manner.

In contrast to the use of spectroscopic measuring systems in the sorting of raw flakes or in polymer melts in an extruder, such spectroscopic measurements for inline process monitoring and, if appropriate, control, have not yet been used in cutter compactor systems on account of the above mentioned limitations, that is to say in the case of hot, softened, but always lumpy, non-melted particulate material particles which moreover swirl rapidly in the container, at a temperature which necessarily changes.

The measuring systems of the physical methods, which are based on the interaction between a physical effect such as, for example, electromagnetic radiation and matter and, for example, analyze the energy spectrum of a sample on the basis of radiation or waves, are essentially volume measuring systems which detect spectra reflected from the material by excitation, for example by laser or infrared light, and either directly evaluate them or compare them with libraries. For this reason, the frequency of the measurements and the recorded "volume range" influence how representative the achieved measurement result is.

One example of such a physical method is Raman spectroscopy. In the following, a few basic features are briefly explained:

In order to be able to apply Raman spectroscopy to molecules, the polarizability must change during rotation or oscillation of the molecule. In Raman spectroscopy, the matter to be analyzed is irradiated with monochromatic light, usually from a laser. In addition to the irradiated frequency (Rayleigh scattering), further frequencies are observed in the spectrum of the light scattered on the sample. The frequency differences with respect to the irradiated light correspond to the energies of rotation, oscillation, phonon or spin-flip processes characteristic of the material. From the spectrum obtained, conclusions can be drawn about the substance under analysis, similar to spectra from infrared spectroscopy. The lines occurring in a Raman spectrum are also referred to as Stokes lines or anti-Stokes lines.

The reason lies in an interaction of light with matter, the so-called RAMAN effect, in which energy is transferred from light to matter ("Stokes side" of the spectrum) or energy from matter to light ("Anti-Stokes side" of the spectrum). Since the wavelength of the light, i.e. its color, depends on the energy of the light, this energy transfer effects a shift of the wavelength of the scattered light relative to the irradiated light, the so-called Raman shift. Among other things, the following material properties can be derived from the spectrum, i.e. the frequency and the associated intensity, and the polarization of the scattered light: crystallinity, crystal orientation, composition, strain, temperature, doping and relaxation.

The RAMAN scattering of molecules normally has a very small scattering cross section of, for example, approximately $10^{-30}$ cm$^2$. The scattering cross-section is a measure of the probability that the molecule to be measured interacts with the incident radiation or the incident particle. Therefore, in the case of small scattering cross sections, a relatively high concentration of molecules or a high laser intensity, i.e. a high number of particles, is necessary in order to obtain a detectable signal. It is therefore not possible for some molecules to obtain RAMAN spectra.

In order to be able to prepare materials such as plastics from different sources and/or with different compositions, so that defined quality characteristics such as mechanical and/or optical properties for reuse are achieved, an analysis of the incoming materials as well as of the processed materials is necessary in addition to the necessary technical machine requirements.

For such an analysis, measuring devices are preferably used, which in particular
- can output absolute values,
- are easy to calibrate, maintain and operate,
- can be integrated into the machine online,
- are robust and designed for 365 days/24 h operation,
- should be integrated into the machine control,
- can flexibly detect different unknown material components.

Furthermore, it should be possible to cover several measuring points on the system with one system and economic aspects such as the costs of a measuring device are also important.

Analysis with RAMAN spectroscopy offers the additional advantages of carrying out absolute measurements and analyses of organic and inorganic components as well as a simple calibration process. Raman spectroscopy also makes it possible to manage with little prior knowledge of the composition of the material to be processed. This is of great importance especially in the post-consumer sector, where it is hardly conceivable to represent all combinations of materials that may occur in real operation in models, which other measurement concepts, however, require as a necessary basis.

Another possibility is the use of near-infrared (NIR) spectroscopy as a physical method for examining, for example, the energy spectrum of a sample on the basis of radiation or waves: Increasing demands on the quality of plastic products, as well as the need to reduce production and preparation costs, require the use of fast and reliable control methods that capture process-relevant quality parameters as early as possible. One method that can do this is fast near-infrared (NIR) spectroscopy.

The measurement setup for NIR spectroscopy can also be implemented with little effort in the industrial environment. No special sample preparation is necessary and the measurement itself is non-destructive. Measurements can be carried out on granules, on powders or else on finished parts.

Furthermore, with this method, the polymer fraction can already be subjected to a quality control in the preconditioning unit PCU or the cutter compactor. This control provides, for example, information about the composition of polymer blends or the moisture content of the plastic. As a result, faulty batches can be avoided and quality characteristics can be continuously documented.

NIR technology is currently only used to a limited extent in the plastics industry, for example in sorting processes. Currently, entrance and exit controls are routinely carried out in the companies. This approach incurs high costs and is time-consuming. In addition to these tests, sample production and preparation are also often necessary. When using RAMAN or NIR technology, sample preparation is advantageously omitted. Furthermore, a statement about the material to be tested can be made simply and within seconds on the basis of a chemometric model produced with the aid of NIR spectroscopy.

Exemplary Embodiments of a Device According to the Invention

It is an object of the invention to provide an inline process control in a production plant or a continuous process monitoring in extrusion plants. It is intended to determine those material properties which can be measured reproducibly with an accuracy sufficient for the user.

Desired properties are, for example:
Moisture
Additive/filler content
Color content qualitatively and quantitatively
Polymer composition, comonomer content
Detection of crosslinking or degree of crosslinking (gelling)

These parameters are to be measured and analyzed. Exemplary embodiments of a device according to the invention for preparing, processing and/or recycling materials, in particular thermoplastic plastic materials, are described below, in which information about these parameters can be obtained inline by means of a physical method such as RAMAN spectroscopy or NIR spectroscopy.

Two exemplary embodiments of a device according to the invention are illustrated in greater detail in FIG. 1 and FIG. 2, as well as in FIG. 3a, FIG. 3b and FIG. 4. As can be seen in FIGS. 1 to 4, the device comprises a receiving container 1 already described above, i.e. a cutter compactor or a preconditioning unit. In the exemplary embodiment shown, the receiving container 1 has a side wall 2, is of cylindrical design and has a lower bottom surface 3. Alternatively, the receiving container 1 can also be formed essentially conical or have a conical or cylindrical wall section.

The receiving container 1 furthermore comprises a mixing and/or comminuting device which is arranged in the vicinity of the bottom 3. In the exemplary embodiment in FIGS. 1 to 4, the receiving container 1 has, as mixing and/or comminuting device, a rotating mixing and/or comminuting tool 4 which can be rotated about a vertical axis of rotation 9. The mixing and/or comminuting tool 4 is used to move and mix, and if necessary, also to heat, comminute and/or soften, the lumpy or particulate material to be treated, wherein in operation a mixing stream is formed in the receiving container 1.

In a receiving container 1 according to the invention, the material is usually present in lumpy or particulate form, for example as ground material or film chips. In this case, such film chips have, for example, a thickness of about 10 μm, wherein it is already possible for individual polymer layers to be present in the film structure here, up to a few mm. The film chips can be imagined as tending to be rather flat structures. The other two dimensions can range from a few mm to about 30 mm to 500 mm. However, they can also be only a few mm. The size is essentially determined by the pretreatment.

The grinding materials can have dimensions from mm to approx. 30 mm to 50 mm. Cubes or ball-like or spherical formations often form. However, dusts or smaller structures such as micro granules or granules can also be used.

It is essential that the materials behave similarly to a fluid and are kept in circulation in the form of a stream by the mixing and/or comminuting tool 4, which has a circumferential speed of approximately 1 m/s to 100 m/s. The circumferential speed of the mixing and/or comminuting tool 4 is preferably selected such that the lumpy or particulate material rotates radially at a speed of 0.3 to 45 m/s and/or in the vertical direction at a speed of 0.1 to 60 m/s.

The material is essentially in the range of 0-80% of the height of the receiving container 1. The material on the outside of the receiving container 1, i.e. e.g. on the side wall 2, has both a direction of movement that is in the circumferential direction and a direction of movement that is primarily also upwards. It is essential that the material on the side wall 2, or on a measuring position located there, is exchanged frequently and regularly.

For example, in the case of film or fiber processing, the material in the receiving container 1 has an average residence time of about 10 to 15 minutes. The material circulates radially at approximately 15 m/s. Accordingly, a certain volume segment will pass the side wall 2 between 40 and 200 times at a measuring position. For this reason, both long-term measurements are possible, i.e. it is integrated during the measurement itself, as well as a large number of measurements in a very short time, i.e. statistical methods can then be used in the evaluation in order to increase the meaningfulness of the measurement, which will be discussed in more detail below.

It can be seen in detail in FIG. 1 that an opening 8 is formed in a side wall 2 of the receiving container 1 for discharge, for example in the region of the height of the mixing and/or comminuting tool 4. The pretreated plastic material is discharged from the interior of the receiving container 1 through this opening 8. If a plurality of mixing and/or comminuting tools 4 are arranged in the receiving container 1, the opening 8 can be arranged in the region of the lowest mixing and/or comminuting tool 4 which is closest to the bottom.

In the exemplary embodiment, a conveyor, for example an extruder 5, with a screw 6 rotating, for example plasticizing or agglomerating, in a housing 16, receives the pretreated material emerging from the opening 8. As in FIGS. 1 and 2, the housing 16 of the conveyor can have a feed opening 80 for the material to be gripped by the screw 6, which feed opening is located at its end face or in its casing wall. This feed opening 80 communicates with the opening 8 through which the material emerges from the interior of the receiving container 1.

A device according to the invention further comprises a spectroscopic and/or spectrometric measuring device 10 for analyzing the lumpy or particulate material moving in the interior of the receiving container 1 or for obtaining information about the respectively measured material, in particular quantitative and/or qualitative parameters of the respective material. This is a measuring device 10 which is based on a previously described physical method for examining the energy spectrum, for example, of a sample on the basis of radiation or waves.

An exemplary embodiment of such a spectroscopic and/or spectrometric measuring device 10 combined with a receiving container 1 is shown in FIGS. 1 to 4. The measuring device 10 measures at least parts of the lumpy or particulate material moving in the interior of the receiving container 1 inline, i.e. during continuous processing operation.

The measuring device 10 of a device according to the invention emits a physical effect, such as, for example, electromagnetic radiation, sound, electrical voltages, or magnetic fields, for exciting at least part of the rotating lumpy or particulate material. In the exemplary embodiment shown, this is brought about by an excitation source 11 acting or directed into the interior of the receiving container 1. Optionally, a plurality of such excitation sources 11 can also be provided.

In the exemplary embodiment shown, an excitation source 11 emits electromagnetic radiation for exciting the material. The measurement signals produced in response to the effect, such as characteristic spectra of the electromagnetic radiation scattered on the measured material, are detected by the measuring device 10. For this purpose, the measuring device 10 comprises at least one detector 12 for detecting the measuring signals arising in response to the effect, in particular characteristic spectra of the electromagnetic radiation scattered on the measured material. In the exemplary embodiment in FIGS. 1 to 4, the detector is a spectroscope 12.

FIGS. 1 and 2 show the structural connection of a RAMAN spectrometer as a measuring device 10 to a receiving container 1 or a preconditioning unit PCU. In this case, a RAMAN probe is connected laterally to the receiving container 1 as a measuring head 24 with a lens system 22, at a height below the usual material level or filling level of the particles moved in the receiving container 1. As can be seen in FIGS. 1 and 2, both the light output for the light emitted by the excitation source 11 and the detection input of the detector 12 for the scattered light from the receiving container 1 are combined in the measuring head 24.

However, the beam path of the light emitted by the excitation source 11 in the direction of the interior of the receiving container 1 and the beam path for the scattered light from the receiving container 1 in the direction of the detector 12 can also be realized separately from one another. It is also possible for the detector 12 to be integrated in the measuring head 24. In this case, the measuring head 24 can be cooled.

Alternatively, for spectroscopic and/or spectrometric analysis of the material in the receiving container 1, the measuring device 10 may also comprise a detector 12 for atomic spectroscopy or molecular spectroscopy, in particular a device for Raman spectroscopy, NIR spectroscopy, UV/VIS spectroscopy, fluorescence spectroscopy and/or absorption spectroscopy.

In the exemplary embodiment in FIGS. 1 to 4, the measuring device 10 further comprises a processing and control unit 40 in data communication with the measuring device 10, specifically the excitation source 11 and the detector 12. On the one hand, the processing and control unit 40 controls the measuring device 10 for emitting the physical effect, in particular for emitting electromagnetic radiation.

On the other hand, the processing and control unit 40 drives the measuring device 10 to detect the resulting measuring signals, in particular the characteristic spectra of the scattered electromagnetic radiation, and to keep the measured values determined in this way available.

As shown schematically in detail in FIGS. 1 and 2, the excitation source 11, the detector 12 and the processing and control unit 40 are coupled to the receiving container 1 in a vibration-free manner via fiber-optic systems and/or light guides 14. The excitation source 11, the detector 12, and the processing and control unit 40 can alternatively also be arranged physically spaced apart from the receiving container 1 or, for example, by means of holding devices on the receiving container 1.

If, for example, a laser is used as the excitation source 11, it is advantageous, as in the exemplary embodiment in FIGS. 1 and 2, to decouple the detector 12 from the receiving container 1 by means of fiber optics. If no fiber optics are used for laser or excitation source 11 and detector 12 (free-beam system), a vibration-free coupling of the sensor system is to be achieved by spacing.

When using fiber optics, it is facilitated to decouple the processing and control unit 40 and the sensor system or the detector 12 from the receiving container 1, which is subject to temperature fluctuations, vibrations, etc. In the exemplary embodiment, the fiber optics is selected in such a way that it has a length of less than 100 m, for example less than 30 m to 50 m, preferably less than 15 m, in order to minimize a corresponding attenuation of the signals and thus advantageously also leads to cost savings, since lower laser intensities are required and the signal-to-noise ratio is improved.

Optical elements and the imaging systems are preferably implemented by suitable measures such as, for example, air purge, dry air, $N_2$ purge, etc. protected against environmental influences such as dust, moisture, temperature, sublimates, etc.

At least one measuring opening 20 is arranged in the receiving container 1, through which the measuring of the materials in the interior of the receiving container 1 is made possible. As can be seen in detail in FIGS. 1 and 2, in the exemplary embodiment it is located in the side wall 2 of the receiving container 1. The physical effect emitted by the excitation source 11, in the exemplary embodiment this is the emitted electromagnetic radiation, acts on the material in the interior of the receiving container 1 through the measuring opening 20.

The measuring opening 20 can have a diameter of 0.5 to 100 mm and can be closed by a window 21 made of a material, for example of sapphire glass, that is transparent for the physical effect such as electromagnetic radiation. Such a window 21 effects an effective separation between the sensor system, i.e. the measuring device 10, and the material to be measured.

In the exemplary embodiment in FIGS. 1 to 4, the measuring opening 20 is arranged in the side wall 2 of the receiving container 1 in the region of the lower third of the height of the receiving container 1. Alternatively, the measuring opening 20 can also be arranged in the region of the height of the lowermost mixing and/or comminuting tool 4 closest to the bottom, in particular somewhat above or below it, preferably outside the narrowest distance between the outermost point of the mixing and/or comminuting tool 4 and the side wall 2.

A preferred construction position of the measuring device 10 is laterally on the receiving container 1, since the shortest distances from the material to be measured can be realized at this position. The distance between the exciting system, i.e. the excitation source 11, such as a laser or an NIR source, and the measuring system, i.e. the detector 12 and the material to be measured, should preferably be as small as possible. In this way, on the one hand, the excitation source 11, i.e. the light sources, can advantageously be kept small, while at the same time a good measurement signal is ensured, since light intensity decreases with $1/r^2$, where r indicates the distance between the detector 12 and the material to be measured.

In the case of the lateral construction on the receiving container 1, the position is preferably selected where the density of the material as well as the pressure on the side wall is highest.

A preferred exemplary embodiment of a method according to the invention for preparing, processing and/or recycling materials, in particular thermoplastic plastic materials, having a measuring device 10, for example a RAMAN spectrometer, arranged on the receiving container 1, i.e. the cutter compactor or the PCU, is described below:

The material to be measured should pass the sensor system of the measuring device 10 at a sufficient frequency, wherein the material has to pass through the focal point 23 of the excitation source 11. In order to focus the electromagnetic radiation of the excitation source 11 onto a focal point 23, a lens or a lens system 22 is provided in the exemplary embodiment, see details in FIGS. 1 and 2. The focal point 23 is located at or directly behind the window 21, preferably at a maximum distance of 10 cm behind the window 21. The higher the contact pressure which the rotating material exerts on the receiving container 1 or a side wall 2 of the receiving container 1, especially in the case of materials with a low bulk density, is at this focal point 23, the higher the intensity of the measurement signal, since the material lies at the focal point 23.

If the focal point 23 were to lie further to the rear, i.e. further inside the receiving container 1 or in the material, scattering effects and reduced intensity would adversely affect the signal and correspondingly decrease the signal-to-noise ratio. For this reason, the lateral installation in the receiving container 1 is advantageous, and preferably, as already described above, in the lower region of the receiving container 1.

It is advantageous if the method is guided in the receiving container 1 in such a way that the level of the material particles or of the mixing stream formed by the movement is held in the receiving container 1 in such a way that it is constantly above the excitation source 11 or the light source.

In a device according to the invention, the material thus constantly covers the window 21 under the operating conditions. This covering also serves to shield from extraneous light in the frequency range from 570 nm to 1008 nm, in particular from 785+/−215 nm, in which the measuring frequencies lie. These are 785+215 nm for the Stokes region and 785−215 nm for the anti-Stokes region, see FIG. 5. The Raman effect results in an energy transfer from the photon (Stokes scattering) to the molecule or from the molecule to the photon (anti-Stokes scattering). Both transitions can be evaluated individually and/or in a ratio to one another. Furthermore, a good stability of the measurement signal during the measurement time can advantageously be achieved in the case of a measurement head 24/window 21 which is largely continuously covered. Optionally, a range of +/−245 nm is also possible, see FIG. 6.

As already mentioned above, the window in the exemplary embodiment in FIGS. 1 to 4 is advantageously formed from sapphire glass in order to allow the relevant frequency spectra to pass in the range from 570 nm to 1008 nm, in particular from 785+/−215 nm. In order to cover applications in the wavelength range of 785 nm, at least the range between 931 nm (Stokes) and 678 nm (anti-Stokes) should be allowed to pass.

In the exemplary embodiment, the surfaces of the window 21 are planar and aligned parallel to one another. Optionally, the inner surface of the window 21 facing the receiving container 1 can also be adapted concavely to the radius of the receiving container 1, and the outer surface of the window 21 facing away from the receiving container 1 can be configured concavely parallel to the inner surface.

As already mentioned above, the excitation source 11 can, as in the exemplary embodiment shown, be a laser with a wavelength range of 100 to 1400 nm, in the range of infrared, visible and/or UV light, e.g. a wavelength range of 780+/−250 nm. Further possible lasers which can be used can cover a wavelength range of 532+/−215 nm, 638+/−215 nm, 820+/−215 nm and/or 1064+/−215 nm.

The laser power is, for example, in the range from 15 mW to 5 W, 100 mW to 500 mW being preferred. The use of lasers with a high energy density is advantageously possible, since the material is constantly exchanged and as a result there is no change in the material to be measured. There may be a particular need for high energy densities, for example in the case of very dark-colored polymers.

Furthermore, attention must be paid to a ratio of laser power to integration time. This is preferably in the range from 5 mW/s to 5000 mW/s, in particular in the range from 15 mW/s to 1000 mW/s.

It is advisable to cool the measuring head 24 of the measuring device 10, which is arranged at the measuring opening 20 or the window 21, with the lens system 22 in order to remain permanently below 90° C., better below 60° C. Gases or liquids can be used as cooling media, but a Peltier element can also be used.

When using near infrared, the conditions described above preferably also apply. In this case, however, the window can also consist of quartz glass in order to allow the relevant frequency spectra in the range from 760 nm to 2500 nm to pass for NIR.

With simultaneous construction of measuring devices 10 based on Raman spectroscopy or near-infrared spectroscopy, fiber optic systems are preferred in order to keep the construction simple. Fiber optic systems require the smallest space immediately in front of the window 21. In this case, it is possible to couple both measuring devices 10 via a window 21, but also via different windows 21. In this case, it has proven to be useful if the windows 21 are located substantially at the same height in the circumferential direction. Local proximity is desirable, but not necessary.

The volume range of the material which can be analyzed is defined by a measurement spot cross-sectional area in the range from 0.1 mm to 5 mm, in particular from 1 mm to 3 mm, and a penetration depth into the material of 0.3 µm to 30 µm. The penetration depth, which in practice leads to good measured values, is in the range from 8 µm to 15 µm. In the exemplary embodiment, the measuring spot cross-sectional area is approximately 1 mm to 3 mm, so that a volume of approximately 0.00015 $mm^3$ can be analyzed. For this reason, the frequency of the measurement or the frequent migration of the material to be measured past the window 21 is important in order to achieve representative measurement results.

Due to the fact that the material in front of the window 21 or in the focal point 23 exchanges frequently and regularly during operation and by means of an adapted frequency of the measurements or by means of the corresponding measurement duration, an extremely high accuracy can be achieved.

On the basis of the measured values determined, the processing and control unit 40 derives information about the respectively measured material, in particular quantitative and/or qualitative parameters of the respective material, and keeps these available. For example, the processing and control unit 40 can spectrometrically and/or spectroscopically analyze the measurement signals arising in response to the effect, in particular of characteristic spectra of the electromagnetic radiation scattered on the measured material.

Process Management and Evaluation

As already described above, the lumpy or particulate material moving in the interior of the receiving container 1 is analyzed or measured inline spectroscopically and/or spectrometrically, and the measured values determined in this way are used to obtain information about the material measured in each case, in particular quantitative and/or qualitative parameters of the material in question. In the exemplary embodiment, the measurement signals produced in response to the electromagnetic radiation are detected and evaluated, preferably spectrometrically, in the form of characteristic spectra of the electromagnetic radiation scattered on the measured material.

The evaluation of the measurement results or spectra thus obtained is carried out by the processing and control unit 40 and is advantageously carried out as follows:

Due to the frequent flow of the material particles past the measuring position or the focal point 23 in the solid to partially softened state, it is possible to use long measuring times which permit the use of, for example, lasers with a low power of approximately 20-200 mW, while the meaningfulness of the measurement results remains sufficiently accurate.

In this case, the processing and control unit 40 controls the measuring device 10 or the excitation source 11 in such a way that it continuously emits the physical effect, for example the electromagnetic radiation emitted by the laser, during a predetermined period of time, e.g. from less than one second to several seconds or one minute or more. Subsequently, the processing and control unit 40 calculates for the respective period of time a single common piece of information about the respectively measured material, i.e. all material particles which have passed through the measuring opening 20 or the window 21 during this period of time and have been detected by the detector 12. Thus, for example, a single sum spectrum can be created for all these material particles.

Alternatively, the processing and control unit 40 can control the measuring device 10 or the excitation source 11 in such a way that it repeatedly emits the physical effect, for example the electromagnetic radiation emitted by the laser, at a plurality of predetermined times. Thus, at each emission, a particle of the material rotating in the receiving container 1 is excited and scatters back radiation which is detected by the detector 12. Subsequently, the processing and control unit 40 can calculate and keep available a mean value of the information about the material measured in each case, on the basis of selected, or all, measured values determined at these times by the measuring device 10, in particular the detector 12, for individual particles. This means that a mean value is formed from a plurality of spectra of individual particles.

Should high/higher laser powers be necessary because of the materials to be measured, the fact that the material is flowing prevents the material to be measured from being influenced by the high energy density of the laser at the focal point 23. Methodically, an unknown material with a higher energy density is excited and the processing and control unit 40 optionally regulates the laser power downwards until the detector 12 is in its linear range. In a static measuring process, this automated measuring process could not be used, since the sample or the material would burn or melt.

Since a temperature change of the material to be processed usually takes place in the receiving container 1, i.e. the cutter compactor or the preconditioning unit, a device according to the invention can optionally also comprise a temperature measuring device 30 which is connected upstream of the processing and control unit 40.

In a conventional mode of operation of the receiving container 1, a temperature change of the material takes place in any case: the material is supplied at room temperature or introduced into the receiving container 1 at the top and is then heated, for example, by the movement of the mixing and/or comminuting tools 4 or by friction. The material becomes hot, softened, but always remains particulate or lumpy and does not melt.

However, this temperature change leads to a change in the spectra recorded by the measuring device 10 or the detector 12 as a result of the structural change in the polymers in this process step. It is therefore advantageous if a corresponding correction is made during the evaluation, especially if the respectively detected spectrum is to be matched against existing spectrum databases.

Such an optional temperature measuring device 30 measures the temperature inside the receiving container 1 and/or the temperature of the material and transmits it to the processing and control unit 40. In this case, for example, the material temperature is detected by means of a temperature sensor which projects into the edge layer of the material and is used as a specification for the correction of the spectra. Alternatively, the container temperature of the receiving container 1 can also be used as the value. A further thermal measuring instrument, for example of an optical nature, can also be mounted correspondingly on the receiving container 1 in order to detect the temperature. In this connection, it is particularly advantageous to place the installation location of the temperature measuring device 30 in local proximity to the window 21 covering the measuring opening 20 or to the measuring head 24 of the measuring device. The temperature measuring device 30 can be arranged in the receiving container 1, for example, at the same height, in particular at the same position, as the at least one measuring opening 20.

The processing and control unit 40 uses the measured values determined by the one temperature measuring device 30 to correct the temperature influence on the information determined for the respectively material measured, in particular the temperature-dependent characteristic spectra of the electromagnetic radiation scattered on the material measured, and keeps the information corrected in this way, in particular spectra, available.

Thus, the temperature information obtained in this way is included in the evaluation and serves as an indication for a temperature correction of the spectra. Thus, for example, the material temperature of the material in the receiving container 1 is measured and sent to the processing and control unit 40. There, the measured actual temperature is used for correcting the spectra, for example to a reference temperature, in order to enable a simple comparison with stored reference spectra. For example, a shift caused by the temperature of the spectra to higher intensities is corrected.

For a particularly simple evaluation of the information obtained for the measured material, such as spectra, the processing and control unit 40 can comprise a memory in which reference information, for example quantitative and/or qualitative reference parameters or reference spectra, are stored. The processing and control unit 40 can then compare the information determined for the respectively measured material, such as spectra, with the reference information, for example reference spectra, and determine the deviation from the reference information or reference spectra. This determined deviation can then be forwarded, for example, to a process control unit and/or a display unit.

The processing and control unit 40 can optionally also cooperate with a process control unit 50 or be in data communication with it. Such a process control unit can use, for example, data transmitted by the processing and control unit 40, i.e. information about the respectively measured material, such as quantitative and/or qualitative parameters of the respective material, for monitoring and/or controlling the process control in the receiving container 1 and/or the subsequent process chain.

Such a process control unit 50 can, e.g., be based on the data transmitted from the processing and control unit 40
- carry out a dosing of fillers into the receiving container 1 and/or with $CaCO_3$. The stamping residues produced during production, but also film residues, therefore have a different polymer content and a different degree of filling.

In order to produce a material of constant quality from these starting materials, it is imperative to know how high the different constituents of filler and/or polymer are. In a compounding step, the end product can now be adjusted to a defined mixture by addition of polymer, additives and filler, provided that the incoming constituents are absolutely known. The flexibility is thereby correspondingly increased. A measurement before and for controlling after the compounding step controls the proportions of the components supplied and thus ensures certain properties and minimizes the costs of production.

Test Setup

In this experimental procedure, an INTAREMA 1180TVEplus comprising a measuring device 10 with a detector 12 for RAMAN spectroscopy and a receiving container 1, i.e. a cutter compactor or a preconditioning unit, was charged with production waste from the production of hygiene film. This material is in the form of lumpy foil sections. Table 1 summarizes the experimental data.

TABLE 1

Experimental data of the first application example

| Material | Machine | PCU Temperature [° C.] | PCU power [kW] | Tool speed [rpm] | Laser intensity [mW] | Integration time [s] | Number of measurements | Measuring time per spectrum [s] |
|---|---|---|---|---|---|---|---|---|
| LDPE + $CaCO_3$ | INTAREMA 1108 TVEplus | 102 | 36-38 | 750 | 200 | 3 | 10 | 30 |

- feed materials, such as polymers, fillers, etc., into the receiving container 1 and/or a discharge device connected to the receiving container 1, and/or
- discharge processed materials, in particular granules, from the receiving container 1 by means of a discharge device, such as the conveyor, connected to the receiving container 1. This will be discussed in more detail below.

APPLICATION EXAMPLES

Example 1

In the following, a first application example of a method according to the invention or of a device according to the invention for preparing, processing and/or recycling of materials, in particular thermoplastic plastic materials, is described:

In the production of hygiene articles such as diapers, sanitary napkins, etc., different polymers with different viscosities and degrees of filling with fillers, such as $CaCO_3$, are used. The nonwoven portion of the hygiene articles usually consists of unfilled PP and the film of LD-PE filled Evaluation Surprisingly, in spite of the above-mentioned high rotational speeds of the particles in the receiving container 1, clear spectra could be registered by the detector 12 or the spectroscope. The spectra detected by the detector 12 are shown in FIG. 7. The spectra show mixtures of PE and varying percentages of $CaCO_3$ (1%, 2%, 5%, 10%, 15%, 17.5%, 20% $CaCO_3$).

The detected spectra are evaluated by the processing and control unit 40 with respect to the proportion of $CaCO_3$, and the proportion of $CaCO_3$ is made available by the processing and control unit 40 in % of the total material.

Interpretation

In the measurement results, the variation of the $CaCO_3$ content in the input material during the process duration of approximately 4 h can be detected, see FIG. 8. Thus, a control signal can be derived to a process control unit 50 connected to the processing and control unit 40, such as a dosing unit, on the basis of which the supply of $CaCO_3$ in powder form or as a master batch is appropriately adapted. In the case of a higher proportion in the input material, the dosing quantity can thus be correspondingly reduced and in the case of a lower proportion in the input material it can be increased. A uniform $CaCO_3$ content is then advantageously present in the end product produced. Usually, a $CaCO_3$ content of approximately 15% to 25% is provided for injection molded products, depending on the application, the deviation being only+/−1% in each case.

Example 2

A second application example of a method according to the invention or of a device according to the invention is described below:

When used packaging materials from the food/non-food sector are reused, the different polymer streams are separated and cleaned as well as possible by sorting and washing processes. In the subsequent thermal forming process (extrusion), both homogenization and melt filtration are carried out. The regenerates produced therefrom must correspond to a certain quality, depending on the application: Thus, for example, for the production of blown film from LD-PE, the proportion of PP should not exceed a certain percentage, since then the desired mechanical properties may not be achieved under certain circumstances or the weldability may no longer be present. Furthermore, since 100% sorting purity can never be achieved in the upstream sorting process, it is useful, for example, to discharge granules from an extruder 5 connected to the receiving container 1 and having a higher PP content. Inline RAMAN measurement makes it easier to determine the PP content in the receiving container 1 and to control the rejection of finished granules if the PP content is too high.

Test Setup

In this experimental procedure, an INTAREMA 80TVE-plus comprising a measuring device 10 with a detector 12 for RAMAN spectroscopy and a receiving container 1, i.e. a cutter compactor or a preconditioning unit, was used. In this experiment, the suitability of a measuring device based on RAMAN spectroscopy, which repeatedly performs measurements at specified time intervals, was demonstrated by adding PE film to a pure PP film in the receiving container 1. For this purpose, in each case two film rolls, a PP roll and an LDPe roll, having a known film width and film thickness, were fed to the receiving container 1 via a separate draw-in value in each case. The percentage distribution was determined mathematically from the weight per unit area and substantiated by random sample testing on the granulate produced. Table 2 summarizes the experimental data.

Evaluation

The spectra detected by the detector 12 are shown in FIG. 9. The spectra show mixtures of PP and PE with varying percentages in each case (100%, 90%, 70%, 50%, 25%, 10% 0% PP).

The detected spectra are evaluated by the processing and control unit 40 and the proportion of the PP is made available by the processing and control unit 40 in % of the total material, see FIG. 10.

Interpretation

By using this measuring process, it is possible to measure the PP content with an accuracy of less than 1% in the material flow. In this way, it is easily possible to control the PP content in the process end product by adding PE material. This is particularly advantageous since it is known from everyday practice that even a proportion of about 5% PP in the LD stream reduces the weldability in such a way that bag production is no longer present.

Example 3

A third application example of a method according to the invention or of a device according to the invention is described below:

PE/PA composites are used as packaging film for foodstuffs. This is a multi-layer structure, in the middle of which is the PA film, which functions as aroma protection, for example. PE (polyethylene) and PA (polyamide) are polymers which do not mix well. However, a very good material for film production or injection molding can be obtained by adding compatibilizers. Since the compatibilizers are very expensive and the proportions of the PA and PE fluctuate, costs can be saved during preparation and the process end product can be optimized if the polymer proportion can be precisely determined and the addition of the compatibilizer can be correspondingly controlled. The residues usually have a proportion of about 40% PA and 60% PE and are present in sheet-like structures, edge strips and film rolls.

Test Setup

In this experimental procedure, an INTAREMA 1108 TE comprising a measuring device 10 with a detector 12 for RAMAN spectroscopy and a receiving container 1, i.e. a cutter compactor or a preconditioning unit, was used. In this experiment, the suitability of a continuous measuring device 10 based on RAMAN spectroscopy was demonstrated by adding the PE/PA edge strips and film pieces to the receiving container 1. In the granulate produced, the corresponding polymer proportions were measured with laboratory measuring instruments to check the proportions previously determined inline. Table 3 summarizes the experimental data.

TABLE 2

Experimental data of the second application example

| Material | Machine | PCU Temperature [° C.] | PCU power [KW] | Tool speed [rpm] | Laser intensity [mW] | Integration time [s] | Number of measurements | Measuring time per spectrum [s] |
|---|---|---|---|---|---|---|---|---|
| PE/PP | INTAREMA 1108 TVEplus | 100 | 40-41 | 750 | 150 | 4 | 10 | 40 |

TABLE 3

Experimental data of the third application example

| Material | Machine | PCU Temperature [° C.] | PCU power [KW] | Tool speed [rpm] | Laser intensity [mW] | Integration time [s] | Number of measurements | Measuring time per spectrum [s] |
|---|---|---|---|---|---|---|---|---|
| PE/PA | INTAREMA 1108 TE | 107 | 48-54 | 750 | 350 | 3 | 10 | 30 |

Evaluation

The spectra detected by the detector 12 are evaluated by the processing and control unit 40 and the proportion of PA to PE is represented by the processing and control unit 40, see FIG. 11.

Interpretation

Due to different variants of the processed films, there are corresponding shifts. Thus, for example, the PE content increases around approx. 9:55. However, this is not desirable in order to achieve a corresponding desired final quality of the process end product, since an excessively low proportion of PA adversely affects the properties of the end product, and in addition too much compatibilizer is added. For this reason, in response to the determined information about the measured material, a diverter can be connected to the end of the treatment plant and the granulate produced can be discharged in the range from 9:55 to 10:08.

The device according to the invention described above or the method according to the invention described above thus makes it possible, using spectroscopic and/or spectrometric measuring devices 10, to carry out effective inline process analysis, process monitoring and, if appropriate, process control in systems for preparing, processing and/or recycling materials, in particular thermoplastic plastic materials, using a receiving container 1, i.e. a cutter compactor or a preconditioning unit PCU.

Furthermore, the information/data transmitted by the evaluation unit can also be used in the subsequent process chain, such as, for example, in the dosing of fillers, the discharge of finished granules, but also in the feeding of other polymers, for example into the receiving container 1, i.e. the cutter compactor or the preconditioning unit PCU.

The invention claimed is:

1. A device for treating, processing, and recycling materials comprising plastic materials, the device comprising:
  at least one receiving container comprising a cutting compactor;
  a mixing and comminuting apparatus for the plastic materials, wherein in each of the at least one receiving container, in a side wall of the receiving container, in a region of a level of a lowermost mixing and comminuting tool closest to a base, an opening is formed through which pretreated plastic materials can be removed from an interior of the receiving container, and in that at least one conveyor comprising an extruder having at least one screw rotating in a housing arranged for receiving the pretreated materials emerging out of the opening;
  a spectroscopic or spectrometric measuring device for analyzing particulate materials moving in the interior of the receiving container and obtaining information comprising at least one quantitative or qualitative characteristic variables of the particulate materials, wherein the spectroscopic or spectrometric measuring device is configured for inline measurement of at least some of the particulate materials moving in the interior of the receiving container, and the spectroscopic or spectrometric measuring device is further configured to:
    emit a physical action comprising electromagnetic radiation for exciting the rotating particulate materials; and
    detect in a spectrometric manner, measurement signals comprising characteristic spectra of the electromagnetic radiation scattered on measured materials, as a reaction to the physical action; and
  a processing and control unit being in data communication with the spectroscopic or spectrometric measuring device, the processing and control unit is configured to control the spectroscopic or spectrometric measuring device to emit the physical action and to detect the measurement signals and to keep available measurement values determined in this manner, and on a basis of determined measurement values to derive the information of respective measured plastic materials, the information comprising the at least one quantitative or qualitative characteristic variables of the particulate materials, and to keep the information available,
  wherein the processing and control unit interacts with, and is in data communication with, a process-control unit, wherein the process-control unit is configured to use the information transmitted by the processing and control unit, the information comprising the at least one quantitative or qualitative characteristic variables of the particulate materials, for monitoring and controlling process management in the receiving container and to use a subsequent process chain.

2. The device of claim 1, wherein the receiving container is arranged as a mixing and comminuting device comprising at least one rotary rotatable about a vertical axis of rotation, wherein the mixing and comminuting tool is for moving, mixing, heating, comminuting, and softening the particulate materials to be treated, and wherein during an operation, a swirl or a mixing vortex is formed in the receiving container.

3. The device of claim 1, wherein a circumferential speed of the mixing and comminuting tool is selected to circulate the particulate materials radially at a speed of 0.3 m/s to 45 m/s and in a vertical direction at a speed of 0.1 m/s to 60 m/s.

4. The device of claim 1, wherein in the receiving container, the housing has an intake opening located on an end face of the housing for the pretreated plastic materials to be gripped by the at least one screw, and the intake opening is in connection with the opening.

5. The device of claim 4, wherein in the side wall of the receiving container, at least one measuring opening is provided to allow the physical action emitted by an excitation source comprising the emitted electromagnetic radiation to act on the rotating particulate materials in the receiving container and scattered light from the receiving container is detected, wherein the measuring opening has a diameter of 0.5 mm to 100 mm.

6. The device of claim 5, wherein the at least one measuring opening in the side wall of the receiving container is arranged in a region of a height of the lowermost mixing and comminuting tool closet to a bottom, at a closest distance between an outermost point of the mixing and comminuting tool and the side wall.

7. The device of claim 5, wherein the at least one measuring opening in the side wall of the receiving container is arranged in a region of a lower third of a height of the receiving container.

8. The device of claim 5, wherein the at least one measuring opening in the side wall of the receiving container is arranged below a filling level of the plastic materials located in the receiving container during operation.

9. The device of claim 1, further comprising a lens or a lens system for focusing the electromagnetic radiation onto a focal point, wherein the focal point is formed on or immediately behind a window at a distance of a maximum of 10 cm behind the window.

10. The device of claim 1, wherein the process-control unit is configured, on a basis of data transmitted by the processing and control unit to make a metered addition of filling materials into the receiving container, to undertake a feeding of materials comprising polymers, into the receiving container and into a discharge device attached to the receiving container.

11. The device of claim 1, wherein the processing and control unit comprises a memory that stores reference information comprising at least one quantitative or qualitative reference characteristics comprising reference spectra, and the processing and control unit is configured to compare information determined for the respective measured materials, comprising the quantitative and/or qualitative characteristic variables, comprising spectra, with the reference information comprising the reference spectra, and to specify a deviation from the reference information, and to forward them to the process control unit or a display unit.

* * * * *